(12) United States Patent
Suga et al.

(10) Patent No.: US 8,580,305 B2
(45) Date of Patent: Nov. 12, 2013

(54) TABLET QUICKLY MELTING IN ORAL CAVITY

(76) Inventors: Tomoharu Suga, Kyoto (JP); Tomio Nakano, Sakai (JP)

( * ) Notice: Subject to any disclaimer, the term of this patent is extended or adjusted under 35 U.S.C. 154(b) by 0 days.

(21) Appl. No.: 10/542,969

(22) PCT Filed: Jan. 20, 2004

(86) PCT No.: PCT/JP2004/000444
§ 371 (c)(1),
(2), (4) Date: Jul. 21, 2005

(87) PCT Pub. No.: WO2004/064810
PCT Pub. Date: Aug. 5, 2004

(65) Prior Publication Data
US 2006/0134199 A1    Jun. 22, 2006

(30) Foreign Application Priority Data
Jan. 21, 2003 (JP) ................................. 2003-012357

(51) Int. Cl.
*A61K 9/42* (2006.01)
(52) U.S. Cl.
USPC ........... 424/476; 424/435; 424/464; 424/465; 424/480
(58) Field of Classification Search
None
See application file for complete search history.

(56) References Cited

U.S. PATENT DOCUMENTS

| 5,464,632 A | 11/1995 | Cousin et al. |
| 5,576,014 A * | 11/1996 | Mizumoto et al. ............ 424/435 |

FOREIGN PATENT DOCUMENTS

| EP | 361874 A2 | 4/1990 |
| EP | 1 405 635 A1 | 4/2004 |
| JP | 8-143473 A | 4/1996 |
| JP | 2001-39861 A | 2/2001 |
| WO | WO 99/44580 | 9/1999 |
| WO | WO 03/072084 A1 | 9/2003 |

OTHER PUBLICATIONS

Supplementary European Search Report.
Wikipedia definition of croscarmellose sodium, Jul. 2, 2013.
Japanese Pharmacopeia, 12th ed. pp. 25-27, Mar. 25, 1991.
C. Dawes, "Circadium Rhythms in Human Salivary Flow Rate and Composition", 220 J. Physiol. 529-545 (1972).

* cited by examiner

*Primary Examiner* — Hasan Ahmed
(74) *Attorney, Agent, or Firm* — Tannenbaum Helpern Syracuse & Hirschtritt LLP

(57) ABSTRACT

The object of the present invention is to provide, as a solid preparation for making it easy to take, thus improving patient's compliance etc., an intraorally rapidly disintegrating tablet which can be produced easily without any particular problem by a usual method of producing tablets with a usual tabletting machine, has practically unproblematic hardness, and disintegrate rapidly in the oral cavity. This tablet is produced by tabletting cores coated with a pharmaceutical disintegrating agent, wherein the core is a granule containing a water-soluble medicament or containing a medicament and a sugar.

7 Claims, No Drawings

TABLET QUICKLY MELTING IN ORAL CAVITY

TECHNICAL FIELD

The present invention relates to an intraorally rapidly disintegrating tablets having practically unproblematic hardness and being rapidly disintegrating in the oral cavity. The phrase "practically unproblematic hardness" refers usually to a hardness of 35 N or more. The phrase "rapidly disintegrating" refers usually to disintegration within 1 minute.

BACKGROUND ART

In recent years, intraorally rapidly disintegrating tablets have attracted attention as the form of a preparation for improving the ability of a chemical to be administered, thus improving patient's compliance etc., and various tablets have been invented.

In consideration of excellent solubility in the mouth, many of conventional intraorally rapidly disintegrating tablets comprise sugar alcohols such as mannitol and xylitol as excipients. However, sugar alcohols easily cause obstacles such as sticking (adhesion to a punch) and binding (adhesion to a die) at the time of tabletting, and hardness is hardly secured. Accordingly, when intraorally rapidly disintegrating tablets are produced by using sugar alcohol as an excipient, a special process and a special apparatus have been employed wherein, for example, a mixture containing sugar alcohol is first moistened suitably with water, then compression-molded under low pressure, dried and thus tabletted.

On the one hand, production of intraorally rapidly disintegrating tablets, which is as close as possible to a usual method of producing tablets by tabletting dry powder or granules, is also devised. For example, a method of producing intraorally rapidly disintegrating tablets which comprises compression-molding a mixture containing a medicament and a disintegrating agent with fine sugar alcohol or sugar having an average particle diameter of 30 μm or less as a major ingredient (see WO 97/47287) and a method of producing intraorally rapidly disintegrating tablets which comprises compression-molding a major ingredient sugar alcohol or sugar not particularly fine, to which a disintegrating agent and cellulose were added (see JP-A 2001-58944), have been anticipated.

However, the techniques described above are common in that dry sugar alcohol is used as a major ingredient, and thus there is necessity for an increase in the content of a highly water-repellent lubricant and for limitation of compression pressure, in order to prevent sticking and binding, and there is a limit to disintegrating properties and hardness.

DISCLOSURE OF INVENTION

The object of the present invention is to provide intraorally rapidly disintegrating tablets which can be produced easily without any particular problem by a usual method of producing tablets with a usual tabletting machine, have practically unproblematic hardness, and disintegrate rapidly in the oral cavity.

They found that cores coated with a pharmaceutical disintegrating agent, wherein the core is a granule containing a medicament, can be tabletted to give an intraorally rapidly disintegrating tablet meeting the object described above, and they completed the present invention.

The present invention includes, specifically, an intraorally rapidly disintegrating tablet characterized by being produced by tabletting cores coated with a pharmaceutical disintegrating agent, wherein the core is a granule containing a water-soluble medicament or containing a medicament and a sugar (hereinafter, the intraorally rapidly disintegrating tablet is referred to as "the tablet of the present invention").

The "sugar" which can be used in the present invention is not particularly limited insofar as it is a pharmaceutically acceptable sugar. The examples of the sugar include sugar alcohols such as mannitol, xylitol, sorbitol, erythritol, maltitol and maltose, lactose, sucrose, glucose, and oligosaccharide. These can be used singly or as a mixture of two or more thereof. Particularly, mannitol and lactose are preferable, and combined use of mannitol and lactose is also preferable.

It can be said that the "pharmaceutical disintegrating agent" which can be used in the present invention is a pharmaceutically acceptable additive capable of promoting disintegration or dispersion of tablet into secondary particles or individual particles with saliva. The disintegrating agent is not particularly limited insofar as it is a disintegrating agent used in pharmaceutical preparations. The examples of the agent include crystalline cellulose, low-substituted hydroxypropyl cellulose, carboxymethyl cellulose (carmellose), calcium carboxymethyl cellulose (carmellose calcium), crospovidone, and starch represented by potato starch, wheat starch, corn starch, rice starch, hydroxypropyl starch (HPS), sodium carboxymethyl starch, and partial-pregelatinized starch (PCS). These can be used alone or as a mixture of two or more thereof. Particularly, corn starch is preferable.

The average particle diameter of the coated granules according to the present invention are not particularly limited, but when a water-sparingly-soluble or water-insoluble medicament is used, the average particle diameter is suitably 20 to 1000 μm, preferably in the range of 30 to 500 μm, more preferably in the range of 50 to 200 μm. The particle diameter is preferably smaller.

The medicament is not particularly limited. The examples of the medicament include the following medicaments. As used herein, the "water-soluble medicament" refers to a medicament which can be dissolved in an amount of not less than 0.5 mg/mL, preferably not less than 1 mg/mL, in water at 20° C.

1. Antipyretic, Analgesic and Antiinflammatory Agents

Indometacin, aspirin, diclofenacsodium, ketoprofen, ibuprofen, mefenamic acid, dexamethasone, sodium dexamethasone sulfate, hydrocortisone, prednisolone, azulene, phenacetin, isopropyl antipyrine, acetaminophen, benzydaminehydrochloride, phenylbutazone, flufenamic acid, sodium salicylate, choline salicylate, sasapirin, clofezone, etodolac, and ferbinac.

2. Antiulcer Agents

Sulpiride, cetraxate hydrochloride, gefarnate, irsogladine maleate, cimetidine, ranitidine hydrochloride, famotidine, nizatidine, roxatidine acetate hydrochloride, and sodium azulene sulfonate.

3. Coronary Vasodilators

Nifedipine, isosorbide dinitrate, diltiazem hydrochloride, trapidil, dipyridamole, dilazep hydrochloride, methyl 2,6-dimethyl-4-(2-nitrophenyl)-5-(2-oxo-1,3,2-dioxaphosphorynan-2-yl)-1,4-dihydropyridine-3-carboxylate, verapamil, nicardipine, nicardipine hydrochloride, and verapamil hydrochloride.

4. Peripheral Vasodilators

Ifenprodil tartrate, cinepazide maleate, cyclandelate, cinnarizine, and pentoxifylline.

5. Antibiotics

Ampicillin, amoxiline, cephalexin, erythromycinethylsuccinate, bacampicillin hydrochloride, minocycline hydrochloride, chloramphenicol, tetracycline, erythromycin, griseofulvin, cefditoren pivoxil, azithromycin, and clarithromycin.

6. Synthetic Antibacterial Agents

Nalidixic acid, piromidic acid, pipemidic acid trihydrate, enoxacin, cinoxacin, ofloxacin, norfloxacin, ciprofloxacin hydrochloride, sulfamethoxazole trimethoprim, 6-fluoro-1-methyl-7-[4-(5-methyl-2-oxo-1,3-dioxolen-4-yl)methyl-1-piperazinyl]-4-oxo-4H[1,3]thiazeto[3,2-a]quinoline-3-carboxylic acid, and itraconazole.

7. Antispasmodic Agents

Propantheline bromide, atropine sulfate, oxapium bromide, timepidium bromide, butylscopolamine bromide, trospium chloride, butropium bromide, N-methylscopolamine methyl sulfate, and methyloctatropine bromide.

8. Antitussive and Antiasthmatic Agents

Theophylline, aminophylline, methyl ephedrine hydrochloride, procaterol hydrochloride, trimetoquinol hydrochloride, codeine phosphate, sodium cromoglycate, tranilast, dextromethorphan hydrobromide, dimemorfan phosphate, clobutinol hydrochloride, fominoben hydrochloride, benproperine phosphate, tipepidine hibenzate, eprazinone hydrochloride, clofedanol hydrochloride, ephedrine hydrochloride, noscapine, carbetapentane citrate, oxeladin tannate, isoaminil citrate, pranlukast, and fluticasone propionate.

9. Bronchodilators

Diprophylin, salbutamolsulfate, chlorprenaline hydrochloride, formoterol fumarate, orciprenaline sulfate, pirbuterol hydrochloride, hexoprenaline sulfate, bitolterol mesilate, clenbuterol hydrochloride, terbutaline sulfate, mabuterol hydrochloride, fenoterol hydrobromide, and methoxyphenamine hydrochloride.

10. Diuretics

Furosemide, acetazolamide, trichlormethiazide, methylclothiazide, hydrochlorothiazide, hydroflumethiazide, ethiazide, cyclopentazide, spironolactone, triamterene, fluothiazide, piretamide, mefruside, etacrynic acid, azosemide, and clofenamide.

11. Muscle Relaxants

Chlorphenesin carbamate, tolperisone hydrochloride, eperisone hydrochloride, tizanidine hydrochloride, mephenesin, chlorzoxazone, phenprobamate, methocarbamol, chlormezanone, pridinol mesilate, afloqualone, baclofen, and dantrolene sodium.

12. Cerebral Metabolism Improving Agent

Mechlophenoxate hydrochloride.

13. Minor Tranquilizers

Oxazolam, diazepam, clotiazepam, medazepam, temazepam, fludiazepam, meprobamate, nitrazepam, chlordiazepoxide, and quazepam.

14. Major Tranquilizers

Sulpiride, clocapramine hydrochloride, zotepine, chlorpromadinone, haloperidol, and risperidone.

15. β-Blockers

Pindolol, propranolol hydrochloride, carteolol hydrochloride, metoprolol tartrate, labetalol hydrochloride, celiprolol hydrochloride, acebutolol hydrochloride, bufetolol hydrochloride, alprenolol hydrochloride, arotinolol hydrochloride, oxprenolol hydrochloride, nadolol, bucumolol hydrochloride, indenolol hydrochloride, thimolol maleate, befunolol hydrochloride, bupranolol hydrochloride, and carbedilol.

16. Antiarrhythmic Agents

Procainamidehydrochloride, disopyramide, ajimaline, quinidine sulfate, aprindine hydrochloride, propafenone hydrochloride, and mexiletine hydrochloride.

17. Antigout Agents

Allopurinol, probenecid, colchicine, sulfinpyrazone, benzbromarone, and bucolome.

18. Anticoagulants

Ticlopidine hydrochloride, dicumarol, and warfarin potassium.

19. Antiepileptics

Phenytoin, sodium valproate, metharbital, and carbamazepine.

20. Antihistaminics

Chlorphenylamine maleate, clemastine fumarate, mequitazine, alimemazine tartrate, and cycloheptadine hydrochloride.

21. Antiemetics

Difenidol hydrochloride, metoclopramide, domperidone, betahistine mesilate, and trimebutine maleate.

22. Antihypertensive Agents

Dimethylaminoethyl Reserpic acid hydrochloride, rescinamine, methyldopa, prazosin hydrochloride, bunazosin hydrochloride, clonidine hydrochloride, budralazine, and urapidil.

23. Sympathomimetic Agents

Dihydroergotamine mesilate, isoproterenol hydrochloride, and etilefrine hydrochloride.

24. Expectorants

Bromhexine hydrochloride, carbocysteine, ethylcysteine hydrochloride, and methylcysteine hydrochloride.

25. Oral Antidiabetic Agents

Glybenglamide, tolbutamide, glymidine sodium, troglitazone, rosiglitazone, pioglitazone hydrochloride, and epalrestat.

26. Cardiovascular System Drugs

Ubidecarenone and ATP-2Na.

27. Iron Preparations

Ferrous sulfate and dry iron sulfate.

28. Vitamins

Vitamin $B_1$, vitamin $B_2$, vitamin $B_6$, vitamin $B_{12}$, vitamin C, and folic acid.

29. Therapeutic Agents for Pollakiuria and Urinary Incontinence

Flavoxate hydrochloride, oxybutynin hydrochloride, terodiline hydrochloride, 4-diethylamino-1,1-dimethyl-2-butynyl (±)-α-cyclohexyl-α-phenylglycolate hydrochloride monohydrate.

30. Angiotensin Converting Enzyme Inhibitors

Enalapril maleate, aracepril, delapril hydrochloride, and candesartan cilexetil.

31. Agent for Treating Nephritis (3β,4α)-3,23-Dihydroxy-N-(2-methoxyethyl)-18β-olean-12-en-28-amide (hereinafter referred to as Compound A).

32. Immune Suppressor

Tacrolimus.

33. Antimalignant Tumor Agents

Paclitaxel, docetaxel, and bicalutamide.

In the "core being a granule containing a medicament and a sugar", the compounding ratio of the medicament to the sugar is determined suitably such that the amount of the sugar is 0.3 to 1000 parts by weight, preferably 0.6 to 500 parts, based on 1 part of the medicament.

The amount of the pharmaceutical disintegrating agent blended varies depending on the particle size of the core, and is not particularly limited insofar as the core is coated therewith, but when the amount is too large, the moldability and the ability of the tablet of the present invention to be administered are affected, and thus the pharmaceutical disintegrating agent is applied preferably in a form as thin as possible onto the whole of the core. The phrase "the core is coated with the pharmaceutical disintegrating agent" refers to a state in which almost all the surface of the core is sealed with the pharmaceutical disintegrating agent.

The amount of the medicament incorporated into the tablet of the present invention can be suitably determined depending on the application method and dose of the medicament to be applied.

In the tablet of the present invention, a third additive can be suitably blended in such a range that the disintegrating property is maintained. The additive includes, for example, a fluidizing agent, a lubricant, a coloring agent, an aromatic, an adsorbent, a stabilizer, an antioxidant, a pH adjusting agent, a surfactant, a buffering agent, a taste corrective, a sweetener, a foaming agent, a preservative, an acidic-taste agent and a tonic, and these additives can be contained in a suitable amount depending on necessity.

The fluidizing agent includes, for example, long-chain fatty acids such as stearic acid; monoglycerides, diglycerides and triglycerides of long-chain (C10 to C22) fatty acids; higher fatty alcohols such as carnauba wax, polyoxyethylene hydrogenated castor oil, stearyl alcohol etc., wax such as cetanol; and lecithins, sodium lauryl sulfate, and these can be contained in an amount of, for example, 20 wt % or less, in the tablet of the present invention. The lubricant includes, for example, stearic acid, magnesium stearate, aluminum stearate, aluminum monostearate, calcium stearate, stearyl alcohol, talc, titaniumoxide, light silicicanhydride, hydrous silicondioxide, magnesium silicate, synthetic aluminum silicate, calcium hydrogen phosphate, sucrose ester of fatty acids, hydrogenated castor oil, hydrogenated rapeseed oil, carnauba wax, beeswax, corn starch, polyethylene glycol, microcrystalline wax, and sodium lauryl sulfate. The lubricant can be contained in an amount of, for example, 3 wt % or less in the tablet of the present invention. The coloring agent includes, for example, iron sesquioxide, yellow iron sesquioxide, titanium oxide and tar dye. The coloring agent can be contained in an amount of, for example, 1 wt % or less in the tablet of the present invention. The aromatic includes, for example, fennel oil, orange oil, cinnamon oil, clove oil, turpentine oil, peppermint oil, eucalyptus oil and lemon oil, and can be contained in an amount of, for example, 3 wt % or less in the tablet of the present invention. The adsorbent includes, for example, light silicic anhydride, calcium silicate, anhydrous calcium phosphate and precipitated calcium carbonate; the stabilizer includes, for example, cyclodextrin and sodium edetate; the antioxidant includes, for example, tocopherol, ascorbic acid and cysteine hydrochloride; the pH adjusting agent includes, for example, phosphate, acetate, carbonate, citrate, tartrate, fumarate and amino acid salt; the surfactant includes, for example, sodium lauryl sulfate, polysorbate 80, polyoxyethylene hydrogenated castor oil and polyoxyethylene (160) polyoxypropylene (30) glycol; the buffering agent includes, for example, ascorbic acid, sodium chloride, potassium chloride and sodium carbonate; the taste corrective includes, for example, lactose, sucrose, glucose, mannitol, fructose, sorbitol, aspartame, saccharine, sodium saccharine, glycyrrhizate, citrate, tartrate, cocoa butter and sodium glutamate; the sweetener includes, for example, sodium saccharine, aspartame, dipotassium glycyrrhizate and stevia (sucrose); the foaming agent includes, for example, sodium bicarbonate and potassium bicarbonate; the preservative includes, for example, benzoate, paraoxybenzoate, salicylate and sodium edetate; the acidic-taste agent includes, for example, citrate, tartrate, malic acid and ascorbic acid; and the tonic includes, for example, menthol, peppermint oil, cinnamon oil, fennel oil and camphor.

The form of the tablet of the present invention is not particularly limited, and the tablet is formed in shapes such as round shapes or odd shapes such as ellipse, doughnut etc. The tablet can be also formed into a scored tablet. The thickness of the tablet is not particularly limited either, but is suitably 1 to 10 mm, preferably 2 to 8 mm. Generally, the tablet is excellent in rapid disintegrating properties as the thickness of the tablet is decreased. The size of the tablet is not particularly limited either, but the minor axis (or the diameter when the tablet is circular) is suitably in the range of 6 to 20 mm, preferably 8 to 12 mm.

The tablet of the present invention can be produced for example by applying the pharmaceutical disintegrating agent in a usual manner onto the core being a granule containing a medicament, then drying it, and tabletting the resulting coated granules in a usual manner with a fluid bed granulating machine.

The core being a granule containing a water-soluble medicament or the core being a granule containing a medicament and a sugar can be produced for example by granulating and drying a medicament, a sugar etc. as the starting materials in a usual manner. The granulation dryer includes, for example, a fluidizing granulation dryer and a tumbling fluidizing granulation dryer.

Coating with the pharmaceutical disintegrating agent can also be conducted after production of the core, but may be conducted by granulating and drying continuously in an analogous manner while the core is produced.

When the core is to be coated with the pharmaceutical disintegrating agent, a pharmaceutically acceptable binder can be added in a suitable amount for the purpose of facilitating the binding of the core to the pharmaceutical disintegrating agent, and addition of the binder is preferable. The binder is not particularly limited insofar as it is used in pharmaceutical preparations. Specific examples include liquid starch glue, methyl cellulose, hydroxypropyl cellulose (HPC-SSL, HPC-SL, HPC-L etc.), hydroxypropylmethyl cellulose, sodium carboxymethyl cellulose (sodium carmellose), gum arabic, gelatin, agar, tragacanth, sodium alginate, pullulan, polyvinyl pyrrolidone, polyvinyl alcohol and polyethylene glycol. These can be used alone or as a mixture of two or more thereof. Particularly, hydroxypropyl cellulose is preferable. Further, sugar such as lactose can also be incorporated into the binder. The binder can be added in the state of solution or slurry.

The method of mixing the respective components is not particularly limited, and can be carried out by using a frequently used mixer.

The method of tabletting is not particularly limited, and the method can be conducted by employing a frequently used rotary tabletting machine, hydraulic pressing machine or single-punch tabletting machine for example. The tabletting pressure is fundamentally not different from the molding pressure in usual tablet production, and is suitably in the range of 3 to 25 $kN/cm^2$, preferably in the range of 8 to 17 $kN/cm^2$. The tablet of the present invention may be produced even if the tabletting pressure is lower than 3 $kN/cm^2$ or higher than 25 $kN/cm^2$, but when the tabletting pressure is too low, the desired hardness of the tablet may not be obtained. On the other hand, when the pressure is too high, tablet hardly rapidly disintegrating in the oral cavity may be obtained.

BEST MODE FOR CARRYING OUT THE INVENTION

Hereinafter, the present invention is described in more detail by reference to the Examples, Comparative Examples and Test Example. As a matter of course, the present invention is not limited to the following examples.

Example 1

6 g of irsogladine maleate, 225 g of D-mannitol (Mannit P, average particle diameter about 60 μm (manufactured by Towa Chemical Industry Co., Ltd.), which is used hereinafter unless otherwise specified) and 159 g of lactose (HMS, average particle diameter about 60 μm, which is used hereinafter) were fed into a fluid bed granulation dryer (MP-01 model (manufactured by Powrex), which is used hereinafter) and granulated while spraying 121.5 g of purified water (binder solution) containing 4.5 g of hydroxypropyl cellulose (HPC-SSL (manufactured by Nippon Soda Co., Ltd.), which is used hereinafter) and 9 g of lactose, thus forming cores, and when the volume of the binder solution was reduced to ⅓, 45 g of corn starch (manufactured by Nihon Shokuhin Kako Co., Ltd. and used hereinafter) was added gradually to the granulation dryer to coat the cores with the corn starch, followed by a drying step, whereby coated granules were obtained. 1.5 g of magnesium stearate (manufactured by Taihei Chemical Industrial Co., Ltd. and used hereinafter) was added to 300 g of the coated granules to give mixed powder which was then tabletted (Correct 12HUK, compression pressure 14.98 kN/cm$^2$ (149.8 MPa) manufactured by Kikusui Seisakusho Ltd. and used hereinafter) into the tablets (300 mg/tablet) of 10 mmφ in diameter according to the present invention.

Example 2

6 g of irsogladine maleate, 225 g of D-mannitol and 159 g of lactose were fed into a fluid bed granulation dryer and granulated while spraying 121.5 g of purified water (binder solution) containing 4.5 g of hydroxypropyl cellulose and 9 g of lactose, and when the volume of the binder solution was reduced to ⅓, 45 g of hydroxypropyl starch (HPS101 manufactured by Freund Sangyo) was added gradually to the granulation dryer, followed by a drying step, whereby coated granules were obtained. 1.5 g of magnesium stearate was added to 300 g of the coated granules to give mixed powder which was then tabletted into the tablets (300 mg/tablet) of 10 mmφ in diameter according to the present invention.

Example 3

6 g of irsogladine maleate, 225 g of D-mannitol and 159 g of lactose were fed into a fluid bed granulation dryer and granulated while spraying 121.5 g of purified water (binder solution) containing 4.5 g of hydroxypropyl cellulose and 9 g of lactose, and when the volume of the binder solution was reduced to ⅓, 45 g of rice starch (Micropearl manufactured by Shimada Kagaku Co., Ltd.) was added gradually to the granulation dryer, followed by a drying step, whereby coated granules were obtained. 1.5 g of magnesium stearate was added to 300 g of the coated granules to give mixed powder which was then tabletted into the tablets (300 mg/tablet) of 10 mmφ in diameter according to the present invention.

Example 4

6 g of irsogladine maleate, 225 g of D-mannitol and 159 g of lactose were fed into a fluid bed granulation dryer and granulated while spraying 121.5 g of purified water (binder solution) containing 4.5 g of hydroxypropyl cellulose and 9 g of lactose, and when the volume of the binder solution was reduced to ⅓, 45 g of fine crystalline cellulose (Avicel PH-101 manufactured by Asahi Kasei Corporation) was added gradually to the granulation dryer, followed by a drying step, whereby coated granules were obtained. 1.5 g of magnesium stearate was added to 300 g of the coated granules to give mixed powder which was then tabletted into the tablets (300 mg/tablet) of 10 mmφ in diameter according to the present invention.

Example 5

6 g of irsogladine maleate, 225 g of D-mannitol and 159 g of lactose were fed into a fluid bed granulation dryer and granulated while spraying 121.5 g of purified water (binder solution) containing 4.5 g of hydroxypropyl cellulose and 9 g of lactose, and when the volume of the binder solution was reduced to ⅓, 45 g of carboxymethyl cellulose (NS-300 manufactured by Gotoku Chemical Company Ltd.) was added gradually to the granulation dryer, followed by a drying step, whereby coated granules were obtained. 1.5 g of magnesium stearate was added to 300 g of the coated granules to give mixed powder which was then tabletted into the tablets (300 mg/tablet) of 10 mmφ in diameter according to the present invention.

Example 6

6 g of irsogladine maleate, 225 g of D-mannitol and 159 g of lactose were fed into a fluid bed granulation dryer and granulated while spraying 121.5 g of purified water (binder solution) containing 4.5 g of hydroxypropylmethyl cellulose (TC-5E manufactured by Shin-Etsu Chemical Co., Ltd.) and 9 g of lactose, and when the volume of the binder solution was reduced to ⅓, 45 g of corn starch was added gradually to the granulation dryer, followed by a drying step, whereby coated granules were obtained. 1.5 g of magnesium stearate was added to 300 g of the coated granules to give mixed powder which was then tabletted into the tablets (300 mg/tablet) of 10 mmφ in diameter according to the present invention.

Example 7

6 g of irsogladine maleate, 225 g of D-mannitol and 159 g of lactose were fed into a fluid bed granulation dryer and granulated while downwards spraying 121.5 g of purified water (binder solution) containing 4.5 g of hydroxypropyl cellulose and 9 g of lactose, and the mixture was subjected to rotating granulation at a rotor revolution rate of 300 rpm. When the volume of the binder solution was reduced to ⅓, 45 g of corn starch was added gradually to the granulation dryer, followed by a drying step, whereby coated granules were obtained. 1.5 g of magnesium stearate was added to 300 g of the coated granules to give mixed powder which was then tabletted into the tablets (300 mg/tablet) of 10 mmφ in diameter according to the present invention.

Example 8

22.5 g of ambroxol hydrochloride, 217.5 g of D-mannitol and 150 g of lactose were fed into a fluid bed granulation dryer and granulated while spraying 121.5 g of purified water (binder solution) containing 4.5 g of hydroxypropyl cellulose and 9 g of lactose, and when the volume of the binder solution was reduced to ⅓, 45 g of corn starch was added gradually to the granulation dryer, followed by a drying step, whereby coated granules were obtained. 1.5 g of magnesium stearate was added to 300 g of the coated granules to give mixed powder which was then tabletted into the tablets (300 mg/tablet) of 10 mmφ in diameter according to the present invention.

Example 9

390 g of D-mannitol was fed into a fluid bed granulation dryer and granulated while spraying 121.5 g of purified water (binder solution) containing 4.5 g of hydroxypropylcellulose and 9 g of lactose, and when the volume of the binder solution was reduced to ⅓, 45 g of corn starch was added gradually to the granulation dryer, followed by a drying step, whereby coated granules were obtained. 3 g of magnesium stearate was added to 300 g of the coated granules to give mixed powder which was then tabletted into the tablets (300 mg/tablet) of 10 mmφ in diameter according to the present invention.

Example 10

390 g of D-mannitol (Mannitol 35, average particle diameter of about 35 μm, manufactured by Roquette Co., Ltd.) was fed into a fluid bed granulation dryer and granulated while spraying 121.5 g of purified water (binder solution) containing 4.5 g of hydroxypropyl cellulose and 9 g of lactose, and when the volume of the binder solution was reduced to ⅓, 45 g of cornstarch was added gradually to the granulation dryer, followed by a drying step, whereby coated granules were obtained. 3 g of magnesium stearate was added to 300 g of the coated granules to give mixed powder which was then tabletted into the tablets (300 mg/tablet) of 10 mmφ in diameter according to the present invention.

Example 11

225 g of acetaminophen, 60 g of D-mannitol and 105 g of lactose were fed in to a fluid bed granulation dryer and granulated while spraying 121.5 g of purified water (binder solution) containing 4.5 g of hydroxypropyl cellulose and 9 g of lactose, and when the volume of the binder solution was reduced to ⅓, 45 g of corn starch was added gradually to the granulation dryer, followed by a drying step, whereby coated granules were obtained. 3 g of magnesium stearate was added to 300 g of the coated granules to give mixed powder which was then tabletted into the tablets (300 mg/tablet) of 10 mmφ in diameter according to the present invention.

Example 12

225 g of precipitated calcium carbonate, 105 g of D-mannitol and 60 g of lactose were fed into a fluid bed granulation dryer and granulated by downwards spraying 121.5 g of purified water (binder solution) containing 2.25 g of polyvinyl alcohol (EG-05 manufactured by Nippon Gosei Kagaku) and 9 g of lactose, and the mixture was subjected to rotating granulation at a rotor revolution rate of 300 rpm. When the volume of the binder solution was reduced to ⅓, 30 g of corn starch and 15 g of carboxymethyl cellulose (NS-300 manufactured by Gotoku Chemical Company Ltd.) were added gradually to the granulation dryer, followed by a drying step, whereby coated granules were obtained. 1.5 g of magnesium stearate was added to 300 g of the coated granules to give mixed powder which was then tabletted into the tablets (300 mg/tablet) of 10 mmφ in diameter according to the present invention.

Comparative Example 1

Direct Tabletting Method

A mixed powder produced by mixing 6 g of irsogladine maleate, 225 g of D-mannitol, 159 g of lactose, 45 g of corn starch and 2.2 g of magnesium stearate was tabletted into comparative tablets (300 mg/tablet) of 10 mmφ in diameter.

Comparative Example 2

Method of Internally Adding a Disintegrating Agent 6 g of irsogladine maleate, 225 g of D-mannitol, 159 g of lactose and 45 g of corn starch were fed into a fluid bed granulation dryer, sprayed with 121.5 g of purified water (binder solution) containing 4.5 g of hydroxypropyl cellulose and 9 g of lactose, granulated and dried to give granules. 1.5 g of magnesium stearate was added to 300 g of the granules to give mixed powder which was then tabletted into comparative tablets (300 mg/tablet) of 10 mmφ in diameter.

Comparative Example 3

Method of Externally Adding a Disintegrating Agent 6 g of irsogladine maleate, 225 g of D-mannitol and 159 g of lactose were fed into a fluid bed granulation dryer, sprayed with 121.5 g of purified water (binder solution) containing 4.5 g of hydroxypropyl cellulose and 9 g of lactose, granulated and dried to give granules. 45 g of corn starch and 1.5 g of magnesium stearate were added to 255 g of the granules to give mixed powder which was then tabletted into comparative tablets (300 mg/tablet) of 10 mmφ in diameter.

Test Example

The hardness of the tablets obtained in the Examples and Comparative Examples, the disintegration time and intraoral disintegration time in a disintegration test were measured. Further, the fluidity (good or not) of the tabletting granules, the binding properties thereof (present or absent), and the adhesion thereof to the surface of a punch (present or absent) at the time of production of tablets were observed.

(Hardness) Measured by using a Monsanto hardness meter. 10 tablets were measured, and the average value was indicated.

(Disintegration time in the disintegration test) Purified water was used as test fluid, and the disintegration time was confirmed according to the item of Tablets in Disintegration test in Japanese Pharmacopoeia, Fourteenth Edition.

(Intraoral disintegration time) The time in which the tablets were disintegrated with only saliva in the oral cavity was measured by 3 male adults (33-, 40- and 53-year-old). The results are shown in Table 1.

TABLE 1

| | Fluidity during tabletting | Tabletting obstacles | | Hardness (N) | Disintegration time (min) | Feel in oral cavity | Disintegration time in oral cavity (sec) |
| | | Creaking | Adhesion to punch | | | | |
| --- | --- | --- | --- | --- | --- | --- | --- |
| Example 1 | good | absent | absent | 44.1 | 0.6 | good | 40-45 |
| Example 2 | good | absent | absent | 49.0 | 0.9 | good | 45-50 |
| Example 3 | good | absent | absent | 54.9 | 1.0 | good | 50-60 |
| Example 4 | good | absent | absent | 62.7 | 0.6 | good | 55-60 |
| Example 5 | good | absent | absent | 40.1 | 0.5 | good | 30-35 |

TABLE 1-continued

|  | Fluidity during tabletting | Tabletting obstacles | | Hardness (N) | Disintegration time (min) | Feel in oral cavity | Disintegration time in oral cavity (sec) |
| --- | --- | --- | --- | --- | --- | --- | --- |
|  |  | Creaking | Adhesion to punch |  |  |  |  |
| Example 6 | good | absent | absent | 40.2 | 1.0 | good | 50-60 |
| Example 7 | good | absent | absent | 43.1 | 0.6 | good | 40-45 |
| Example 8 | good | absent | absent | 46.1 | 1.0 | good | 35-40 |
| Example 9 | good | absent | absent | 45.1 | 1.0 | good | 35-40 |
| Example 10 | good | absent | absent | 51.0 | 1.0 | good | 35-40 |
| Example 11 | good | absent | absent | 50.0 | 0.6 | good | 40-45 |
| Example 12 | good | absent | absent | 42.1 | 0.9 | good | 40-50 |
| Comparative Example 1 | bad | present | present | 18.6 | 0.7 | — | — |
| Comparative Example 2 | good | present | absent | 20.6 | 0.8 | — | — |
| Comparative Example 3 | bad | present | present | 35.3 | 0.8 | — | — |

As described above, the tablets of the present invention could be produced excellently without tabletting obstacles, had hardness without any practical problem, and were disintegrated rapidly in the oral cavity.

The invention claimed is:

1. An intraorally rapidly disintegrating tablet obtained by tabletting a coated granule which consists essentially of:
a core consisting of an active ingredient mixed with at least one sugar, a coating of a starch substantially completely covering said core to form the coated granule, and a pharmaceutically acceptable binder for adhesion of the coating to the core, wherein the average particle size of the granule is in the range of 50 μm to 200 μm, and wherein the tablet disintegrates in the oral cavity within 1 minute.

2. The intraorally rapidly disintegrating tablet according to claim 1, wherein the sugar is selected from the group consisting of sugar alcohol represented by mannitol, xylitol, sorbitol, erythritol, maltitol and maltose; lactose, sucrose, glucose, and oligosaccharide.

3. The intraorally rapidly disintegrating tablet according to claim 1, wherein the thickness of the tablet is in the range of 1 to 10 mm.

4. The intraorally rapidly disintegrating tablet according to claim 1, wherein the starch selected from the group consisting of potato starch, wheat starch, corn starch, rice starch, hydroxypropyl starch, sodium carboxymethyl starch, and partial-pregelatinized starch.

5. An intraorally rapidly disintegrating tablet obtained by tabletting a coated granule which consists essentially of:
a core consisting of a water soluble active ingredient, a coating of a starch substantially completely covering said core to form a granule, and a pharmaceutically acceptable binder for adhesion of the coating to the core, wherein the average particle size of the granule is in the range of 50 μm to 200 μm, and wherein the tablet disintegrates in the oral cavity within 1 minute.

6. The intraorally rapidly disintegrating tablet according to claim 5, wherein the starch is selected from the group consisting potato starch, wheat starch, corn starch, rice starch, hydroxypropyl starch, sodium carboxymethyl starch, and partial-pregelatinized starch.

7. The intraorally rapidly disintegrating tablet according to claim 5 wherein the thickness of the tablet is in the range of 1 to 10 mm.

* * * * *